United States Patent [19]

Gigante

[11] 4,248,807
[45] Feb. 3, 1981

[54] METHOD FOR MAKING A DENTURE

[76] Inventor: John Gigante, 600 Hilltop Ter., Cliffside Park, N.J. 07010

[21] Appl. No.: 35,650

[22] Filed: May 3, 1979

Related U.S. Application Data

[63] Continuation-in-part of Ser. No. 840,154, Oct. 7, 1977, Pat. No. 4,161,065.

[51] Int. Cl.$^3$ .......................... A61C 13/04; B29C 5/04
[52] U.S. Cl. ..................................... 264/18; 264/278; 264/311
[58] Field of Search .................. 264/16, 18, 311, 259, 264/271, 278, 277; 249/54; 425/425, 430; 433/168; 260/31.8 M; 525/70, 80, 193

[56] References Cited

U.S. PATENT DOCUMENTS

| | | | |
|---|---|---|---|
| 2,120,006 | 6/1938 | Strain | 264/331 |
| 2,558,139 | 6/1951 | Knock et al. | 264/16 |
| 2,618,031 | 11/1952 | Mazer | 264/311 |
| 2,848,750 | 8/1958 | Sannecke et al. | 264/17 |
| 2,851,734 | 9/1958 | Schnell et al. | 264/17 |
| 3,234,169 | 2/1966 | Taub | 260/31.8 |
| 3,419,891 | 9/1966 | Cornell | 260/31.8 |
| 3,427,274 | 2/1969 | Cornell | 260/31.8 |
| 3,969,303 | 7/1976 | Prosen | 260/31.8 C |
| 4,022,855 | 5/1977 | Hamblen | 264/311 |
| 4,104,333 | 8/1978 | Lee | 260/31.8 M |

Primary Examiner—W. E. Hoag
Attorney, Agent, or Firm—Leonard W. Suroff

[57] ABSTRACT

The present invention relates to a method for use in creating a prosthetic denture device such as a denture component formed of a set of hard teeth bonded within an adjustable frame assembly. The frame assembly may be completely or substantially formed having adjustable frame portion which is formed from a composition that is centrifugally cast, and which when cured becomes rigid but not completely polymerized and therefore capable of being subsequently remolded with finger pressure when elevated in temperature. In this manner the adjustable frame portion is remoldable and conformable to desired portions of the oral cavity in the creating of an artificial denture.

25 Claims, 18 Drawing Figures

U.S. Patent  Feb. 3, 1981  Sheet 1 of 3  4,248,807
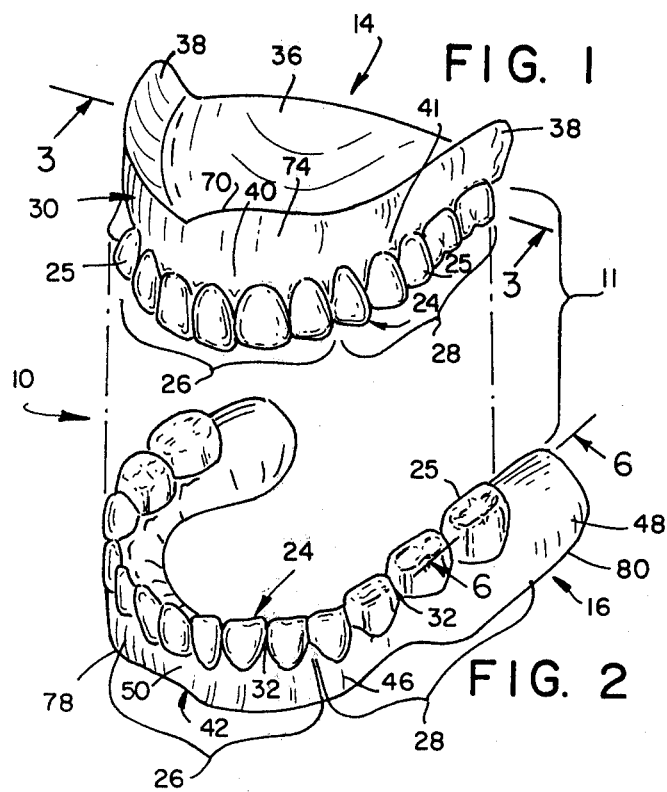
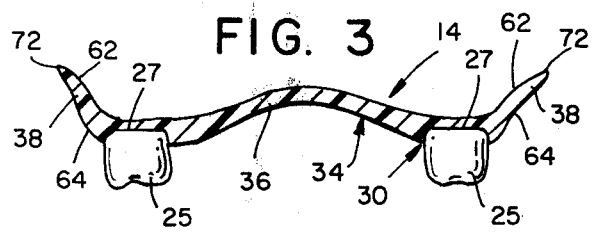
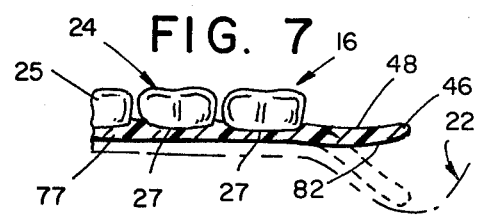
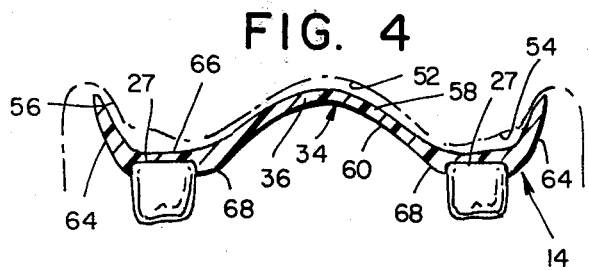
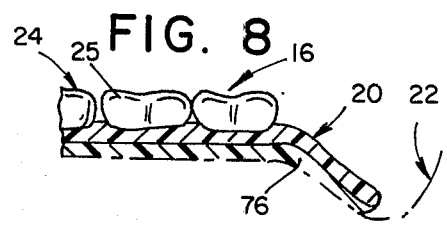
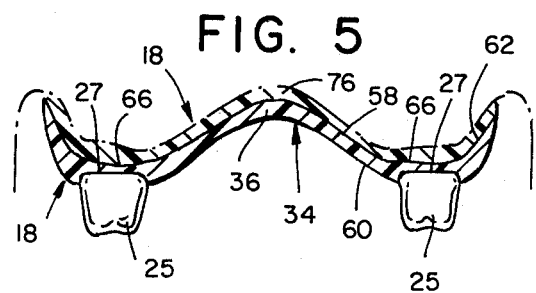

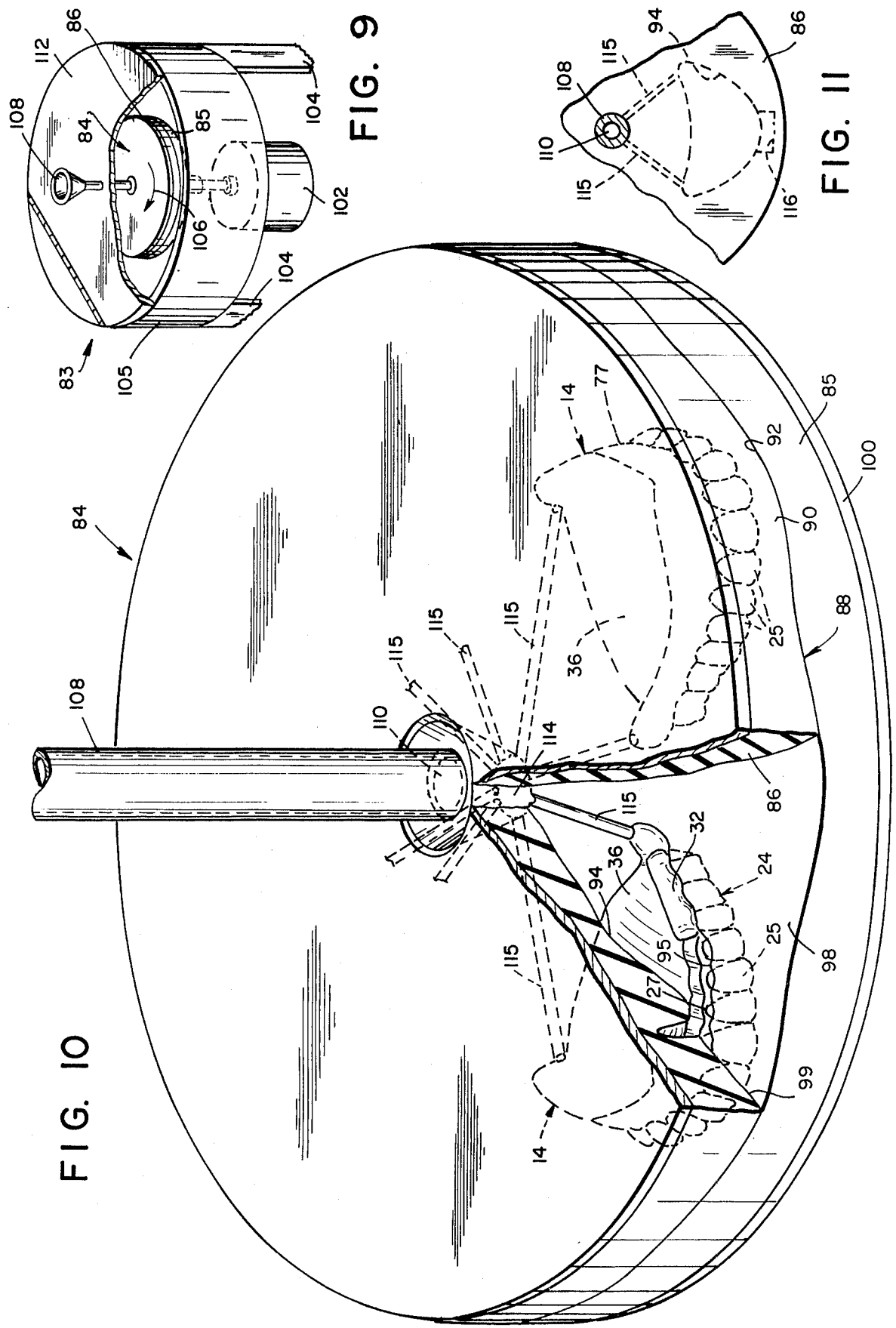

METHOD FOR MAKING A DENTURE

CROSS REFERENCE TO RELATED APPLICATION

This application is a continuation-in-part of co-pending patent application of the same inventor, Ser. No. 840,154 filed Oct. 7, 1977 now Pat. No. 4,161,065, which entire subject matter of the co-pending application is incorporated herein by reference as if fully set forth herein.

BACKGROUND OF THE INVENTION

1. Field of The Invention

The present invention relates to an article or assembly for use in creating artificial dentures, and more particularly of the type that the dental profession may adapt to the patient's mouth at a single sitting if desired.

2. Description Of The Prior Art

There are many people who have lost their natural teeth and who, for economic and other reasons, are unable to obtain prosthetic or artificial denture replacements through the services of professional dentistry. It has been appreciated in the prior art that the time and costs associated with providing a set of dentures to a patient could be substantially reduced if a portion of the artificial or prosthetic denture was previously manufactured and the final fitting to the patient's mouth took place during one or two dental visits. By providing to the dental profession an article that has been previously manufactured on a mass production basis, and that only requires a final fitting to a respective patient, the advantages and cost savings of a mass produced product can be passed along to the patient.

One form of prior art device is illustrated in U.S. Pat. No. 3,727,309, issued to Elbert P. Huey, and discloses a denture having certain characteristics to permit the dentist or other trained technician to perform certain adjustments while the denture is situated within the oral cavity of the prospective denture user. Huey appreciates that an assembly having a rigid structure to support the teeth and a flexible portion which could be deformed by finger pressure would permit the necessary adjustment to the curvature or configuration of the edentulus ridge in the maxillary area of the patient's mouth, for example.

The present inventor has discovered that the utilization of certain chemical compositions in casting a denture it is possible to form a frame assembly that upon adjustment thereafter remains substantially rigid even when the wearer is consuming liquids of approximately 140° F. or less. This feature provides a major advantage in the denture art over the device disclosed in U.S. Pat. No. 3,727,309.

Another form of prosthetic denture is disclosed in U.S. Pat. No. 3,839,796, issued to James M. Hazar, and discloses a denture to be individually fitted to the patient's mouth with a minimum of time involvement by the dentist. The present inventor has found that substantial improvement is obtained over the invention disclosed in U.S. Pat. No. 3,839,796 by providing a palatal vault member which when brought into conformable relationship with the palatal vault of the patient remains set in its selected position even when subsequently exposed to conventional elevated temperatures.

In the Hazar patent a palatal member is initially pressure molded having a specific configuration. This configuration is subsequently reheated by the dentist or other licensed denture delivery person, to remold the palatal member to conform to the palatal portion of the patient being fitted with dentures. It has been found that the palatal vault member manufactured in accordance with the teachings of U.S. Pat. No. 3,839,796 has a memory to it such that when subsequently subjected to heated liquid above about 140° F., there is a softening thereof. Hot coffee for example can exceed 140° F. Accordingly, upon this reheating, the palatal vault member desires to return to its original configuration, and this has proven to be a drawback to the denture disclosed in Hazar U.S. Pat. No. 3,839,796.

The present invention should not be confused with the disclosure in U.S. Pat. No. 2,685,133, issued to B. N. Greene et al, in which the inventors' desire to provide a system wherein the individual who is remote from a dentist may perform those steps necessary to obtain the impression required to manufacture the dentures.

OBJECTS OF THE INVENTION

An object of the present invention is to provide an article for use in creating a denture which can be fitted by the dentist in a minimum of time, avoiding delays due to frequent fitting appointments with the patient.

Another object of the present invention is to provide a novel article for use in producing a prosthetic denture and methods and apparatus of manufacturing the article and prosthetic denture.

Another object of the present invention is to provide a prosthetic denture which includes an article having a frame assembly with a set of teeth extending therefrom in dentally operative position and the frame assembly having an adjustable frame portion which may be remolded by the dentist.

Another object of the present invention is to provide an article for use in creating a prosthetic denture device and a novel method and apparatus for spin casting of a chemical composition adjacent to a set of teeth previously positioned in a mold for producing the article.

Other objects and advantages of the present invention will become apparent as the disclosure proceeds.

The present invention is adapted to provide the dentist with a greater degree of flexibility in producing a denture for the patient, and the various advantages and distinctions of my invention over the prior art will become more clearly evident as the disclosure proceeds.

In addition, up to the present invention the method and apparatus of manufacturing prosthetic devices to form artificial dentures have essentially been along conventional lines as that associated with dental laboratory procedures well known in the art. These procedures have been most satisfactory when producing individual sets of customized dentures, but they are not economically feasible for large production runs. The present invention also sets forth a system for manufacturing large production runs of denture assemblies in an efficient and economical manner.

SUMMARY OF THE INVENTION

The outstanding and unexpected results obtained by the practice of the method and apparatus of this invention are obtained by a series of features, steps and elements assembled and working together in interrelated combination.

In accordance with one aspect of the present invention, an article for use in creating a prosthetic denture device is formed of a set of hard teeth either individually positioned within or interconnected within a frame assembly. The set of teeth extending from the frame assembly in dentally operative position. The frame assembly may include an initially rigid hard frame portion so as to couple the teeth to each other in the mould during fabrication of the denture device.

The adjustable frame portion is generally integrally joined to the set of teeth and is formed from a composition curable at about room temperature but being capable of being subsequently remolded with finger pressure either at elevated temperatures of 140° F. to 150° F. In this manner the adjustable frame portion is remoldable and conformable to desired portions of the oral cavity in the creating of an artificial denture.

The novel article and denture of the present invention is fabricated by placing a set of artificial teeth in a mold having a spaced continuous cavity along the base portion of the teeth. The teeth may be individually positioned within the mold or first coupled to each other at one end thereof and inserted within the mold as an assembly. By employing a moldable composition having the property that when cured at room temperature it becomes rigid but a temperatures of about 140° F. to 150° F., the composition is capable of being subsequently remolded with finger pressure, the beneficial results are obtained.

By filling the non-teeth portions of the cavity with the composition and then curing the composition in the cavity, the set of teeth are integrally joined together with the composition. In this manner it is possible to obtain an initially rigid frame assembly or structure from which the teeth depend, whereby in producing the artificial denture the portion of the frame assembly fabricated from the moldable composition is plyable when elevated in temperature by finger pressure to closely conform the composition to desired portions of the oral cavity and permit the obtainment of a shifting of the individual teeth to suit the needs of the denturer wearer.

In this manner the denture can be readily adjusted such that the anterior and posterior teeth may be individually adjusted in the composition when the contour of the frame assembly is determined.

The apparatus for manufacturing an article used in dentistry, such as an artificial denture of the like, in accordance with the present invention, includes a mold separable into two sections and having at least one cavity therein. A set of artificial teeth are supported in the cavity in a dentally operative relationship to each other, and means for rotating the mold with the set of artificial teeth positioned therein is provided. In addition means for providing access to the cavity as the mold is rotating so as to cause a flow of a material into the cavity such that a centrifugally cast frame is formed with the teeth depending therefrom is also provided. The rotating of the mold is at approximately 675 R.P.M., and the mold includes a plurality of individual cavities connected from a substantially central position such that a centrifugal casting of one frame in each of the cavities is formed.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

FIG. 1 is a perspective view illustrating a maxillary article for use in creating a set of prosthetic dentures in accordance with the present invention;

FIG. 2 is a perspective view illustrating a maxillary and mandibular article for use in creating a set of prosthetic dentures in accordance with the present invention;

FIG. 3 is a sectional view taken along lines 3—3 of FIG. 1 illustrating the maxillary article prior to positionment in the oral cavity;

FIG. 4 is a view similar to FIG. 3 illustrating the change of contour of the palatal vault area and the tuberosity heels to be brought into conformal relationship with the edentulus ridge in the maxillary area of the patient's mouth;

FIG. 5 is a view similar to FIG. 4 illustrating the application of a liner to the upper surface of the maxillary article to form a prosthetic denture;

FIG. 6 is a sectional view taken along lines 6—6 of FIG. 2;

FIG. 7 is a sectional view illustrating the change of contour of the retromolar pad area as it is brought into conformal relationship with the area of the patient's mouth;

FIG. 8 is a view similar to FIG. 7 illustrating the application of a liner to the surface of the mandibular article to form a prosthetic denture;

FIG. 9 is a perspective view of apparatus in accordance with the present invention for centrifugal casting of denture related articles in accordance with the present invention;

FIG. 10 is an enlarged perspective, partly broken away and in section, illustrating the separable sections of the mold in which the articles are formed;

FIG. 11 is an enlarged fragmentary top plan view illustrating the flow of material to each cavity in the mold;

DESCRIPTION OF PREFERRED EMBODIMENTS

Figure 12:
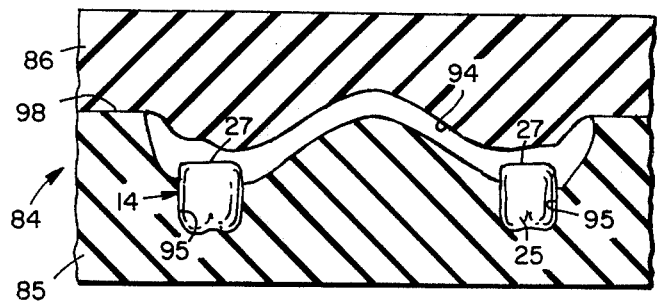
FIG. 12 is a cross-sectional view of the mold assembly illustrated in FIG. 10, utilized in the fabrication of a maxillary denture.

Referring to the drawings in detail, there is illustrated in FIGS. 1 through 17 the procedure and apparatus for both fabricating and converting one or more articles 10 into a set of prosthetic dentures 11. To form the dentures 11 there is initially fabricated a maxillary or upper denture frame or article 14 and a mandibular or lower denture frame or article 16, which may be subsequently processed, in a manner hereinafter described, to form a maxillary or upper denture device 18 and a mandibular or lower denture device 20. The novel construction of the articles 14 and 16 permits selective adjustment of portions thereof to provide a customized fit to the contour of the oral cavity 22 of a particular patient.

The maxillary article 14 is comprised of a set 24 of hard teeth which may be cast or molded from an acrylic resin. Other rensins are also suitable, provided they have the necessary combination of properties as hardness, stain resistance, impact strength, non-flow (noncreep) and resistance to body fluids and foods. They must also be non-toxic and non-irritating to membranes and have color stability. A set of teeth 24 is associated with articles 14 and 16 and include individual teeth 25. Each set 24 is divided into an anterior group or segment 26 and a posterior group or segment 28. Each tooth 25 has a base portion 27 which is embedded or contained below the exposed surface of the denture articles 14 and 16. A set of teeth 25 in accordance with the present invention, may include only an anterior group 26, posterior groups 28, or both groups.

Article is to be utilized in creating a maxillary prosthetic denture device which is readily fitted in a customized fashion to the oral cavity 22 of the patient. Although the article 14 may be manufactured in various sizes such as small, medium and large, as well as tapered or oval configurations, it is necessary to select an article and remold certain portions thereof in order to obtain the customized fit desired.

Accordingly, the set 24 of hard teeth may be contained in a frame assembly 30, which might include a portion 32 into which all, or substantially all, of the teeth 25 may be contained. The set of teeth 24 is positioned in dentally operative relation to each other. Separate or all portions of the frame assembly 30 may be designed to act as an adjustable frame portion 34. The adjustable frame portion 34 is integral with the portion 32 forming part of the upper frame 14. The portion 32 may even be flexible, if used, to initially couple the teeth together when they are set into the mold as hereinafter described. The portion 32 may be flexible and set as a band so as to permit a full set of teeth 24 to be positioned in the mold at one time. As illustrated in FIG. 1, the palatal vault area 36, as well as the tuberosity heels 38, have been fabricated from the adjustable frame portion 34. In addition, the anterior portion 40 and the posterior portions 41 of the frame assembly 30 may be also fabricated within an adjustable frame portion 34.

In this manner with respect to the maxillary article 14, one or more sections thereof may be fabricated from an adjustable frame portion 34 which, as hereinafter explained, is conformable to selective areas of the oral cavity 22. The adjustable frame portion 34 preferably constitutes substantially all of the maxillary article 14, except for the teeth 25, although only selective portions may be fabricated from an adjustably deformable material.

The construction of the mandibular denture 18 may be similarly constructed such that a frame assembly 42 has contained therein a set of teeth 24. The set of teeth 24 may be divided into an anterior segment 26 and a posterior segment 28 extending on each side thereof. The frame assembly 42 includes an adjustable frame portion 46 into which all of the teeth 25 may be set. The retromolar pad areas 48 are fabricated as part of the adjustable frame portion 46. In addition, the anterior portion 50 may also be fabricated as part of the adjustable frame portion 46. As illustrated in FIGS. 3 through 5, the maxillary article 14 is to be brought into conformal relationship with the palatal vault area 52, toothless human gum area 54, and tuberosity heel portion 56.

The palatal vault area 36 includes the upper or inner surface 58 and a lower or outer surface 60. Similarly, the tuberosity heels 38 include an inner or upper surface 62 and a lower or outer surface 64. The frame assembly 42 is similarly provided with an upper or inner surface 66 and a lower or outer surface 68 from which the set of teeth extends downwardly in a generally U-shaped configuration.

The inner surface 66 is adapted to generally receive the toothless gum area 54 of the oral cavity 22. The frame assembly 30 includes an upper terminal edge or ridge 70 which may blend with the upper terminal edge or ridge 72 of each of the tuberosity heels 38. The upper terminal edge 70 defines the upper extremity of the vertically extending wall portion 74 which extends upwardly from the set of teeth 24 and the rigid frame portion 32.

In accordance with the present invention the frame portion 34 of the maxillary article 14, and the frame portion 46 of the mandibular article 16, are selected to be formed from a moldable composition 77 which is cured at room temperature to become rigid but is capable of being subsequently remolded with finger pressure at elevated temperatures, e.g. about 140° F. to 150° F. The composition becomes rigid again upon lowering the temperature to room temperature and remoldable again upon raising the temperature thus allowing a number of adjustments by the dentist or operator to conform the denture to a person's mouth.

The plastic materials advantageously used in the composition 77, to obtain the novel denture articles 14 and 16, are hereinafter described in detail.

With particular reference to FIG. 4, the maxillary article 14 has now had the adjustable frame portion 34, particularly the palatal vault portion 36 and tuberosity heels 38, contoured to a desired configuration. By virtue of the moldable composition of this invention the adjustable frame portion of the article will be softened by placing it in a liquid such as water in the temperature range of 140° F. to 150° F. This step may be carried out exteriorly of the oral cavity 22, in that the dentist may first view the contour of the oral cavity 22 and conform the palatal vault area 36 and tuberosity heels 38 to a desired contour. In addition the vertically extending wall portion 74 is also adjustable.

In this manner the first step of forming the article 14 into the maxillary denture 18 occurs in that the palatal vault area 36 becomes resilient at a temperature which is preferably about 140° F. and capable of being set in a reformed position from that as shown in FIG. 3. After the article 14 is cooled, as by quenching in water at room temperature or below, the adjustable frame portion 34 becomes rigid.

In this manner the palatal vault area 36, formed from the adjustable frame portion 34, may be deflected upwardly into various positions depending upon the geometry of the palatal vault of a given patient. Since the preferred temperature for the composition 77 to be deformed is approximately 140° F. to 150° F., the finger pressure by the dentist is generally applied when the article 14 is not within the mouth of the patient. Upon cooling of the palatal vault area 36, tuberosity heel areas 38 and wall portion 74, they will remain in a set position in close conformity with the geometry of the respective oral cavity 22.

Accordingly the adjustable frame portions 34 and 46 which are formed from the composition 77, becomes rigid when cured at room temperature, but are capable of being subsequently remolded with finger pressure when elevated in temperature. In this manner the adjustable frame portions 34 and 46 are remoldable and conformable to desired portions of the oral cavity 22 in the creating of an artificial denture. The novel set of articles 10 require in the manufacturing thereof the selecting of the composition 77 having the properties which when cured becomes rigid but is not completely polymerized.

Therefore the composition 77 is capable of being subsequently remolded with finger pressure when elevated in temperature, and upon cooling becoming substantially rigid, but thereafter moldable if subsequently raised to a preselected elevated temperature. In this manner several adjustments of the adjustable frame portions 34 and 36 may take place until the desired fit for a particular patient is obtained.

As illustrated in FIG. 5, the final fitting of the maxillary article 14 occurs in that a liner 76 of plastic material, well known in the art, is applied to the contiguous upper surfaces 58, 62 and 66. The liner 76 is of a relatively soft material until cured, such that it very accurately conforms with the features of the maxillary surfaces 52, 54 and 56 of the oral cavity 22.

The maxillary article 14, as illustrated in FIGS. 1 and 3, now has a recontoured configuration, as illustrated in FIG. 5. These changes in contour may be in one or more areas, for example the palatal vault area 36 and the tuberosity heels 38. When the liner 76 is formed on the upper surfaces 58, 62 and 66, the resultant maxillary denture 18 is now fabricated and ready to be worn by the user.

It has been found desirable to have the ability to alter the exact alignment or positionment of one or more of the teeth 25 forming the anterior segment 26 or posterior segment 28. In accordance with the present invention, this ability is provided by molding the anterior segment 26 and posterior segment 28 within an anterior portion 40 and posterior portion 41 fabricated from the composition 77 so as to form adjustable frame portions 34 and 46.

At such time as the denture article 14 is elevated in temperature, the teeth 25 forming the anterior portion 26 as well as the posterior portion 28, may be changed as to their positionment relative to each other, or they may be left in the exact position as they are initially manufactured. The present invention permits the flexibility to customize the dentures 18 and 20 produced in accordance with the facial configuration of the user or if only one denture is made then with the shape of the existing teeth.

FIGS. 6 through 8 illustrate the progressive steps of custom fitting the article 16 so as to form the mandibular denture 20 having the liner 76 thereon to fit the human gum area. The mandibular article 16 terminates in a free end 78 that merges with the outer or free end 80 of the retromolar pad areas 48. It has been found that the retromolar pad areas 48, having an inner or upper surface 82, generally require adjustment relative to the associated area of the oral cavity 22. As illustrated in FIG. 7, the retromolar pad area 48 may be reformed to a desired configuration. This is accomplished during the period of time that the mandibular article 16 is raised to an elevated temperature such that the composition 77, hereinafter discussed in detail, is raised to the requisite temperature in order to remold same with finger pressure. The remolding may occur when the mandibular article 16 is contained exteriorly of the oral cavity 22.

As illustrated in FIG. 8, the liner 76 is thereafter applied in its soft uncured state to obtain the final fitting over the mandibulary ridge of oral cavity 22, in order to form the mandibular denture 16. In this embodiment the anterior segment 26 may similarly be set in an anterior portion 40 fabricated from material of the composition 77. As explained with respect to the maxillary denture 18, this permits selective positionment of the individual teeth 25 contained in the anterior segment 26 and posterior segment 28.

The manufacturing process as to produce the articles 14 and 16 in accordance with the present invention may be varied, but a preferred form of equipment is illustrated in FIGS. 10 through 17. FIGS. 10-12 illustrates a preferred form of apparatus 83 for centrifugal casting of the composition 77 to form the complete frame of either the denture article 14 or 16. The apparatus 83 utilizes a mold or mold assembly 84 which has a lower mold or section 85 and an upper mold or section 86 with aligning means 88, which may be in the form of individual elements 90 adapted to be received in wells 92. The lower mold 85 may include a continuous cavity 94 with means for supporting the individual teeth therein, such as pockets or recesses 95 adapted to receive a set 24 of the individual teeth 25 therein. The cavity 94 extends below the upper surface 98 of the lower mold 85 and may also extend within the upper mold 86, above the lower surface 99 thereof.

FIG. 10 illustrates that the individual teeth 25 may be positioned within the respective pockets or recesses 95 formed in the lower section 85, such that the distal end or base portion 27 of each tooth 25 extends above the surface 98 of the lower section 85. The extent to which the base portion 27 of the tooth extends above the mold section 85 permits the composition 77 to contain the base portion 27 so as to obtain a rigid coupling between the teeth 25 and the frame portions 34 and 46 when they are at room temperature. The teeth 25, which may be linked together by a molded portion 32 or some other coupling element, are still free to be individually adjusted when the article 10 is raised to an elevated temperature, as disclosed herein.

Each tooth 25 has its base portion 27 that extends within the cavity 94. The molds 85 and 86 may be fabricated from silicone rubber or other similar materials, but yet having a certain degree of flexure, in order to permit the undercut portions of the cavity 94 to have the contained portions of article 14 therein removed therefrom. It is appreciated that molds may be used of metal or other materials provided that removal of a cured article 14 or 16 may be removed therefrom. Certain plastic compositions may also be used.

Figure 15:
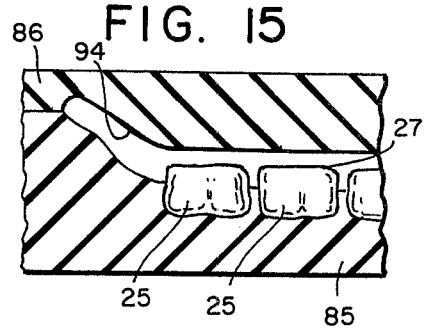
FIG. 15 is a cross-sectional view of the mold assembly illustrated in FIG. 10, when utilized in the fabrication of a mandibular denture.
Figure 13:
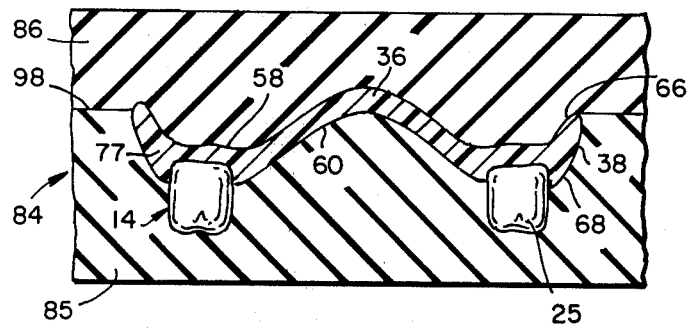
FIG. 13 is a sectional view similar to FIG. 12 illustrating the flow of a moldable composition according to the invention within the cavity of the mold by centrifugal casting.
Figure 16:
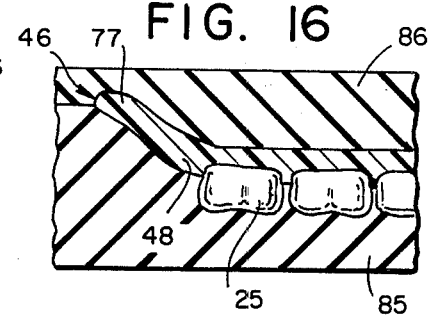
FIG. 16 is a sectional view similar to FIG. 15 illustrating the flow of a composition within the cavity of the mold by centrifugal casting.
Figure 14:
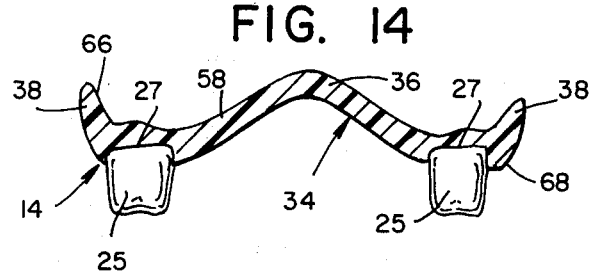
FIG. 14 is a sectional view of the maxillary denture as it is removed from the mold.
Figure 17:
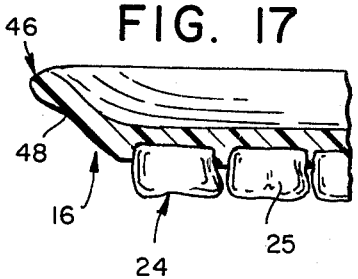
FIG. 17 is a sectional view of the mandibular denture as it is removed from the mold.

Although a maxillary article 14 is illustrated with respect to the manufacturing procedures illustrated in FIGS. 10, 12 and 13 a mandibular article 16 may be fabricated in a similar manner as illustrated in FIGS. 15 through 17.

With particular reference to FIG. 12, there is illustrated the method of fabricating the article 14 by utilizing the molds 85 and 86 and placing the set 24 of artificial teeth 25 along the sockets 95 provided therefor. In this embodiment the set of teeth 24 may be initially fabricated as a subassembly outside of the mold assembly 84 and inserted therein prior to casting the composition 77. In the alternative the teeth 25 may be first molded in the recesses 95 and the composition 77 poured or positioned on the teeth 25 while the teeth 25 are contained in the mold assembly 84 as illustrated with respect to FIG. 18.

The moldable composition 77, which is used to form the adjustable frame portion 34, which may include the palatal vault area 36, tuberosity heels 38 and wall portion 74 is added to selected portions of the cavity 94. The viscosity of the composition 77 is such that it may selectively flow into respective portions of the cavity 94.

In this manner the complete article 14 is such that curing or hardening of the composition takes place within the mold assembly 84, in order to form the desired frame assembly 30. The hardening or curing of the composition in the mold 84 takes place at about room temperature. At elevated temperatures of about 140° F. to 150° F. the initially rigid frame assembly 30 is rendered readily remoldable with finger pressure and is conformable to the oral cavity of the person's mouth.

The moldable composition is formed by the combination of a polymeric powder blend and a plasticized liquid acrylic monomer mixture.

The polymeric powder blend comprises a polyvinyl acetate-based polymer and a homopolymer of ethyl methacrylate. The polyvinyl acetate-based polymer comprises from about 15% to 25% of the weight of the blend and the ethyl methacrylate comprises from about 75% to 85% by weight. The polyvinyl acetatebased polymer can either be a copolymer of polyvinyl chloride and polyvinyl acetate containing about 85% polyvinyl chloride and about 15% polyvinyl acetate or a homopolymer of polyvinyl acetate. The copolymer of polyvinyl chloride and polyvinyl acetate is preferred since it enhances the tensile strength and improves the impact resistance of the hardened moldable composition. The polyvinyl acetate homopolymer on the other hand, enhances the mixing properties of the blend.

A peroxide catalyst, preferably benzoyl peroxide, is added to the polymeric powder blend in amounts of from 0.5 to 2% by weight of the total blend. Such catalyst promotes free radical polymerization of the monomers in the liquid plasticized monomer mixture as will be described hereafter.

The blend of polyvinyl acetate-based polymer and homopolymer ethyl methacrylate is formed by ball-milling the materials to form an intimate powdered blend. The catalyst may thereafter be blended or it may be added to the polymer components and blended in one step. Coloring materials such as pigments and dyes may also be blended into the powder, if desired.

The plasticizer liquid acrylic monomer mixture comprises ethyl methacrylate in amounts of from 80% to 85% by weight and isobutyl methacrylate in amounts of from 15% to 20% by weight. A plasticizer, preferably butyl phthalyl butyl glycolate, is added to the monomers in an amount of from 5% to 10% by weight of total monomers. Other plasticizers such as dibutyl phthalate, butyl benzyl phthalate, dimethyl phthalate, dicyclohexyl phthalate, diisodecy phthalate, dioctyl phthalate, butyl phthalyl butyl glycolate, isodecyl diphenyl phosphate, alkyl benzyl phthalate, and mixtures thereof can also be employed. An amine activator such as dimethyl paratoluidine is also added in an amount of from 0.5 to 2% by weight of the total monomer.

The polymeric powder blend and plasticized liquid acrylic monomer mixture are combined with stirring for example, to form the moldable composition. Generally the blend to monomers weight ratio should be from about 2:1 to about 2:15.

The monomers and blend are self-cured at room temperatures, e.g. 60° F. to 80° F. in about 7 to 12 minutes and must therefore be added to the cavity 94 within such time. However, as previously mentioned, the so-formed composition is remoldable at temperatures of from 140° F. to 150° F. after curing.

By virtue of the moldable composition, the adjustable frame portions 34 and 46 may be deformed one or more times before a final setting is reached. Due to the temperatures at which the second composition is deformable, which is approximately 140° F. to 150° F., the dentist would first place the article 14 or 16 in heated water such that the adjustable frame portions 34 and 46 soften to the point where they are remoldable by finger pressure. The dentist would remold portions such as the palatal vault area 36, tuberosity heels 38, or retromolar pad areas 48, after visually inspecting the oral cavity to determine the amount of adjustment required. At the same time that the frame portions 34 or 46 are softened, the teeth 25 may be shifted or repositioned such that the anterior segment 26 or posterior segment 28 may be customized to the facial configuration of the prospective wearer.

The moldable composition is such that the dentist can fit the remolded article into the patient's mouth to check the quality of the fit after remolding. If a second adjustment is required, the process may then be repeated a second or third time so as to obtain a closer adjusted fit.

Further, the moldable composition has basically no "memory" in that there is no tendency for it to return to an original configuration, which is a deficiency with dentures formed by the prior art teachings. The liner 76, which may be fabricated from impression materials well known in the dental art, is then poured over the upper surfaces of the article 14 or 16 and the final impression is made. The liner 76 is curable by conventional dental procedures.

FIG. 9 through 11 illustrate the spin casting apparatus 83 that may be utilized to obtain the completed denture articles 14 or 16. Prior to the utilization of apparatus 83, considerable amounts of hand labor were required in order to obtain the finished product. The ability to utilize the product 10 has considerably advanced the art and provides a technical breakthrough in the manufacture of denture components. The apparatus 83 is such that the mold sections 85 and 86 may be fabricated from silicone rubber and are produced so that they may withstand usage over prolonged periods of time.

The set of teeth 24 may be fabricated earlier and inserted within the lower section 85, prior to positioning the upper section 86, in overlapping relationship thereto utilizing the aligning means 88. The mold assembly 84 may then be positioned within the apparatus 83 on a table 100 which is adapted to be rotated at a speed of approximately 675 RPM by a motor 102. The apparatus 83 includes a plurality of legs 104 and a frame 105 which has the mold assembly 84 positioned therein.

As the table 100 is rotated, as indicated by arrow 106, the composition 77 is continuously poured through a funnel 108 into the mold assembly 84 through a center opening 110 in the top 112 of the casting machine 83.

The composition 77 flows, by gravity, into the center sprue 114 and through the runners 115 in the mold assembly 84 to the individual cavities 94. Spin cycle time is determined according to the curing characteristics of the composition 77. It has been determined that the room temperature curing of the composition takes place within the mold assembly within 9 to 12 minutes.

In this manner, at the end of the spin cycle, which may vary from nine to twelve minutes, the denture article 14 or 16 is cured and ready to be packaged for shipment. Obviously, any flash as well as the runners are removed in a conventional manner.

Although four cavities 94 are easily filled simultaneously, it is appreciated that more or less may be utilized in each mold assembly 84. It has been found preferable that two runners 115, as illustrated in FIG. 11, be utilized to obtain an equalized centrifugal flow of the composition 77 within each cavity 94. There may also be provided an enlarged area or pocket 116 into which escapted air may flow.

The resultant product 14 or 16 does not require further polishing, which has in prior processes resulted in extensive hand labor which appreciably increased the cost of the product and further was deleterious as to the appearance thereof.

The denture articles illustrated herein may either be fabricated into a complete denture assembly, as illustrated in FIGS. 5 and 8 with a liner thereon, or they may be utilized in a manner which is called the "two step procedure". This procedure is such that the denture assembly with the impression therein is sent to a dental laboratory and by using conventional techniques the teeth of the denture article are "jumped", such that a newly formed denture using the impression previously taken is utilized to form a finalized product. In this manner a relining is obtained such that the original composition and the original rigid liner are substantially removed and replaced by another composition in order to form a complete denture. This other composition is selected to be compatible with the original composition and conforming to the contour of the original rigid liner. There is then a curing of the other composition and the original composition in a conventional manner for creating a prosthetic denture. The denture components of the present invention are adaptable for either mode of operation.

Figure 18:
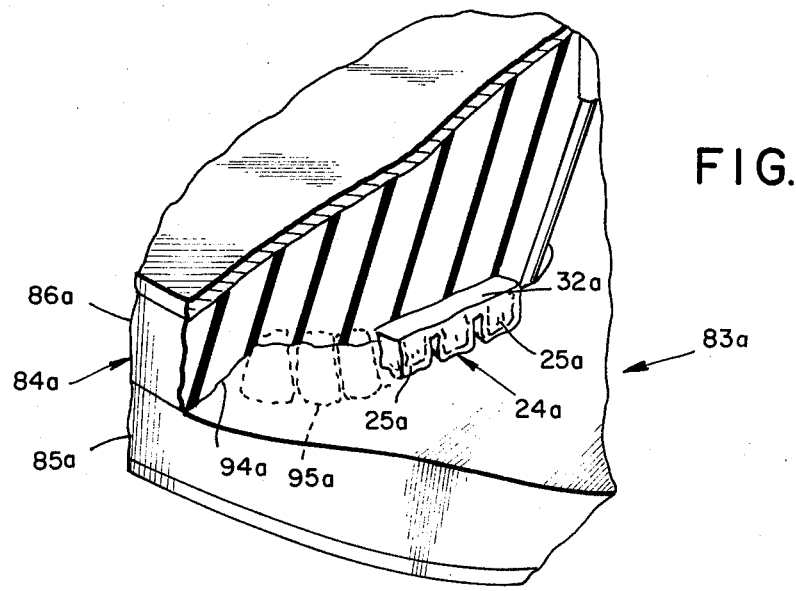
FIG. 18 is a fragmentary view of the mold assembly when used to form teeth therein.

FIG. 18 illustrates another embodiment of the present invention wherein the spin casting apparatus 83a may be utilized to form the set of teeth 24a concurrently such that all of the teeth 25a are molded from a selected composition and fabricated as a complete assembly. Accordingly, the mold assembly 84a may have a lower section 85a and an upper section 86a. The lower section 85a is provided with a plurality of cavities or pockets 95a, each pocket being of a size for a respective tooth 25a to be formed therein during the spin casting procedure which is similar to that described above.

The set of teeth 24a may be fabricated with a flexible linking or coupling member 32a, such that a set of teeth 24a may be removed as an assembly from the lower section 85a. If desired the set of teeth 25a may be then repositioned in a different lower mold section 85a that is as illustrated with respect to FIG. 10. In that assembly the composition may then be spin cast therein and the desired denture article formed. In the alternative, the set of teeth 25a may be left in the mold in which it was formed and a new upper section 86a may be coupled thereto so as to provide a cavity 94a necessary to form the frame of the article.

Whichever procedure is followed, the casting of the frame would then take place with the desired composition. The importance in having the ability to spin cast the individual teeth is that by having them linked together it is possible to easily handle from mold to mold, thereby further dimensioning the labor involved in the fabrication of the article as disclosed herein.

Furthermore, by having the teeth formed within a mold section and then merely moving the mold section to a different machine, or using the same machine and changing the matching section, the final product is the article itself, and there is no handling of the teeth on an individual basis.

It must be fully appreciated that the market for fabricated dentures is great throughout the world, and this invention permits the reduction of cost so as to provide potential users with a set of dentures at substantially reduced fees throughout the world.

Although illustrative embodiments of the invention have been described in detail herein with reference to the accompanying drawings, it is to be understood that the invention is not limited to the precise embodiments, and that various changes and modifications may be effected therein without departing from the scope or spirit of the invention.

I claim:

1. A method for manufacturing an article used in producing an artificial denture comprising the steps of:
   A. positioning a set of teeth formed from individual teeth in a mold having a cavity associated therewith, said teeth each extending at one end thereof partially within said cavity,
   B. rotating said mold;
   C. adding to said rotating mold a moldable composition so as to fill said cavity and enclose said one end of each of said teeth, said composition comprising a polymerizable mixture of a polyvinyl acetate-based polymer and ethyl methacrylate homopolymer powder blend and a plasticized liquid acrylic monomer mixture comprising ethyl methacrylate and isobutyl methacrylate and a plasticizer, and
   D. curing said composition in said cavity to integrally join said composition together with said set of teeth and to form said artificial denture, said composition being remoldable at elevated temperatures so as to selectively conform to desired portions of an oral cavity and said teeth being individually adjustable in said composition to desired positions.

2. The method of claim 1, including the steps of:
   a. individually positioning said teeth in said mold, and
   b. releasably retaining said teeth in said mold with said one end exposed within said cavity so as to embed said teeth therein such that the article formed is a denture assembly from which said teeth depend.

3. The method of claim 1, including the step of maintaining said rotating of said mold until said adding of said composition into said mold has been completed.

4. The method of claim 1, wherein said catalyst is benzoyl peroxide.

5. The method of claim 1, including the step of heating said denture to a deforming temperature in the range of 140° F. to 150° F. to provide said composition to be readily remoldable with finger pressure and conformable to the oral cavity of a person's mouth.

6. The method of claim 1, wherein said step of curing said composition in said mold occurs at about room temperature.

7. The method of claim 1, wherein said polymer blend comprises from about 15% to 25% by weight of said polyvinyl acetate-based polymer and from about 75% to 85% by weight of said ethyl methacrylate homopolymer.

8. The method of claim 1, wherein the weight ratio of said polymeric powder blend to said plasticized liquid acrylic monomer mixture of said composition is from about 2:1 to 2:1.5.

9. The method of claim 1, including the step of positioning at least a portion of said set of teeth in the anterior segment of said composition, whereby an adjustment of said anterior teeth may be obtained when said assembly is heated and said composition reaches its deforming temperature.

10. The method of claim 1, wherein said mold is provided with a plurality of pockets adapted to have said individual teeth positioned therein in frictional engagement with said pockets such that said teeth are contained within said mold during said rotating thereof.

11. The method of claim 1, wherein the said set of teeth are temporarily coupled to each other prior to adding said composition to said cavity.

12. The method of claim 1, wherein said frame structure is to be formed into a maxillary artificial denture having a palatal vault area thereon, said palatal vault area being formed from said composition.

13. The method of claim 1, wherein said rotating of said mold is at approximately 675 R.P.M.

14. The method of claim 1, further including the step of selecting a time period for said rotating of said mold, whereby said curing of said composition occurs during rotating thereof.

15. The method of claim 1, wherein said polymerizable polymer blend contains a free-radical forming catalyst.

16. The method of claim 5, including the steps of:
a. opening said mold, and
b. separating said assembly from said mold.

17. The method of claim 1, wherein said polyvinyl acetate based polymer is a homopolymer of polyvinyl acetate or a copolymer of polyvinyl acetate and polyvinyl chloride.

18. The method of claim 17, wherein said copolymer comprises about 15% polyvinyl acetate and 85% polyvinyl chloride.

19. The method of claim 1, including the steps of:
a. providing a plurality of cavities in said mold, and
b. connecting said cavities to each other by at least one sprue so as to permit a flow of said composition to each of said cavities from a central position thereby centrifugally casting said composition in each of said cavities.

20. The method of claim 19, including the steps of:
a. utilizing a mold separable into two sections, and
b. forming each one of said cavities so as to partially communicate with said sections.

21. The method of claim 1, wherein said plasticized liquid acrylic monomer mixture comprises from 80% to 85% by weight of said ethyl methacrylate monomer and from 15% to 20% by weight of said isobutyl methacrylate.

22. The method of claim 21, wherein said plasticizer is butyl phthalyl butyl glycolate.

23. The method of claim 21, wherein said plasticizer comprises from 5 to 10% by weight of said monomer mixture.

24. The method of claim 21, wherein said monomer mixture further comprises an amine activator.

25. The method of claim 24, wherein said amine activator is dimethyl paratoluidine.

* * * * *